United States Patent
Smith et al.

(10) Patent No.: US 7,912,541 B2
(45) Date of Patent: *Mar. 22, 2011

(54) BIOFEEDBACK ELECTRONIC STIMULATION DEVICE USING LIGHT AND MAGNETIC ENERGY

(75) Inventors: Timothy Brooks Smith, Dallas, TX (US); Tammy Jane Smith Lahutsky, Plano, TX (US); Woodrow W. Baker, II, Nacogdoches, TX (US); Terryl Everett Biggs, Addison, TX (US)

(73) Assignee: Avazzia, Inc., Dallas, TX (US)

(*) Notice: Subject to any disclaimer, the term of this patent is extended or adjusted under 35 U.S.C. 154(b) by 847 days.

This patent is subject to a terminal disclaimer.

(21) Appl. No.: 11/747,458

(22) Filed: May 11, 2007

(65) Prior Publication Data
US 2007/0225769 A1    Sep. 27, 2007

Related U.S. Application Data

(63) Continuation-in-part of application No. 11/203,387, filed on Aug. 12, 2005, now Pat. No. 7,509,165.

(60) Provisional application No. 60/799,995, filed on May 12, 2006.

(51) Int. Cl.
*A61B 5/04* (2006.01)
(52) U.S. Cl. .................... 607/2; 607/50; 607/62
(58) Field of Classification Search .............. 607/2, 46, 607/48, 65, 88, 89, 94, 95, 100, 103, 115; 128/907
See application file for complete search history.

(56) References Cited

U.S. PATENT DOCUMENTS

| | | | |
|---|---|---|---|
| 4,105,017 A | | 8/1978 | Ryaby et al. |
| 4,112,923 A | * | 9/1978 | Tomecek ................. 600/11 |
| 4,266,532 A | | 5/1981 | Ryaby et al. |
| 4,266,533 A | | 5/1981 | Ryaby et al. |
| 4,998,532 A | | 3/1991 | Griffith |
| 5,014,699 A | | 5/1991 | Pollack et al. |
| 5,304,207 A | * | 4/1994 | Stromer ................... 607/3 |
| 5,723,001 A | | 3/1998 | Pilla et al. |
| 5,974,342 A | * | 10/1999 | Petrofsky .................. 607/50 |
| 6,221,095 B1 | * | 4/2001 | Van Zuylen et al. .......... 607/88 |
| 6,249,698 B1 | * | 6/2001 | Parris ..................... 607/3 |
| 6,745,078 B1 | | 6/2004 | Buchner |
| 7,198,633 B1 | * | 4/2007 | Starwynn ................ 607/90 |
| 7,503,927 B1 | * | 3/2009 | Vetanze ................. 607/91 |
| 2004/0267333 A1 | | 12/2004 | Kronberg |
| 2007/0129759 A1 | | 6/2007 | Colthurst |

* cited by examiner

*Primary Examiner* — Carl H Layno
*Assistant Examiner* — Gary A Porter, Jr.
(74) *Attorney, Agent, or Firm* — Howison & Arnott, L.L.P.

(57) ABSTRACT

A biofeedback stimulation device includes a user interface for providing at least one input signal. A processor generates at least one control signal responsive to the at least one input signal. Circuitry within the biofeedback stimulation device enables application of both an electric stimulation signal and a light stimulation signal to a body of an individual. The application of the electrical stimulation signal and the light stimulation signal are controlled by the at least one control signal provided by the processor.

21 Claims, 8 Drawing Sheets

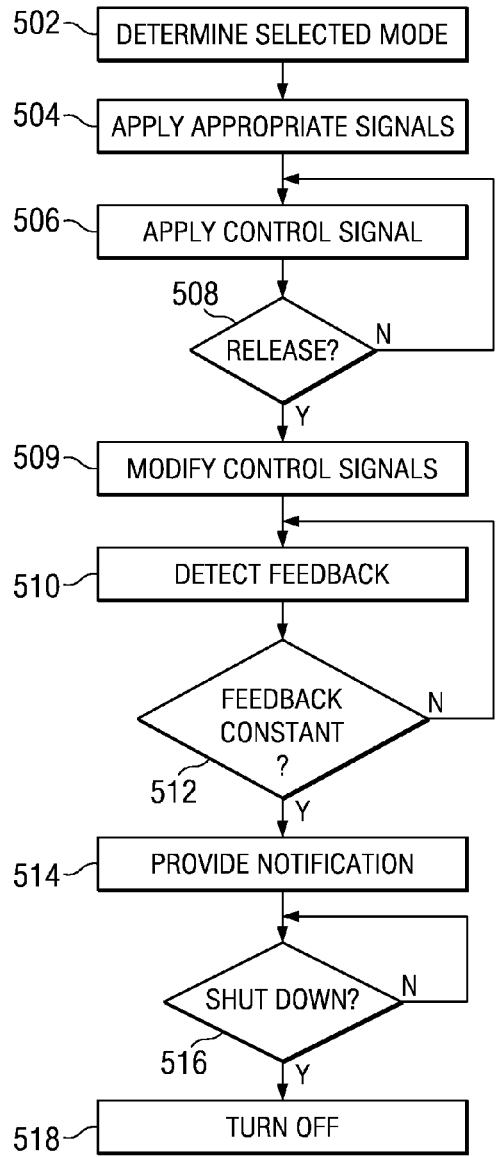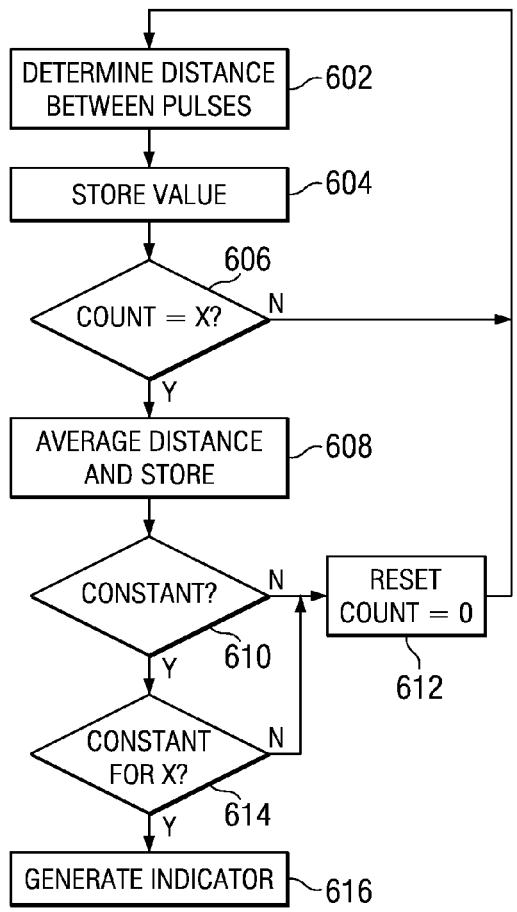

BIOFEEDBACK ELECTRONIC STIMULATION DEVICE USING LIGHT AND MAGNETIC ENERGY

CROSS-REFERENCE TO RELATED APPLICATIONS

This application claims priority from U.S. Provisional Application Ser. No. 60/799,995, filed May 12, 2006, entitled BIOFEEDBACK ELECTRONIC STIMULATION DEVICE USING LIGHT AND MAGNETIC ENERGY, and is a continuation in part of U.S. patent application Ser. No. 11/203,387, now U.S. Pat. No. 7,509,165, filed Aug. 12, 2005 entitled BIOFEEDBACK ELECTRONIC STIMULATION DEVICE, which is incorporated herein by reference.

TECHNICAL FIELD

The invention relates to the field of pain management systems, and more particularly, to biofeedback stimulation devices and the use of photonic and magnetic radiation simulation.

BACKGROUND

There are many people with injuries and ailments that are related to energy. Examples include sprained ankles, carpal tunnel syndrome, arthritis, and numbness of extremities like neuropathy, stroke, and neurology conditions such as ADD and macular degeneration. These are all ailments that the human body must work to recover from. They are not viruses or infections or other chemically related ailments. They are not instances where surgery has proven effective such as reattaching bones or ligaments or other body parts, or clearing arteries.

Energetic medicine addresses these energy related ailments. There has been much research into energetic medicine, and the way the body's electric and nervous system works dating back to the 1900s. Devices have been developed such as the Rife machine, Beck's Box, infrared light therapies, and magnetic therapies used in energetic medicine. There are diagnostic tools such as MEAD machines, which measure resistance in the body's energetic pathways called energy meridians. There are treatment machines in the category of TENS and electronic acupuncture.

SUMMARY

The present invention, as disclosed and described herein, on one aspect thereof, comprises a biofeedback stimulation device. The biofeedback stimulation device includes a user interface for providing at least one input signal. A processor generates at least one control signal responsive to the at least one input signal. Circuitry enables an application of both an electrical stimulation signal and a light stimulation signal to a body of an individual, wherein the application of the electric stimulation signal and the light stimulation signal are controlled by the at least one control signal.

BRIEF DESCRIPTION OF THE DRAWINGS

For a more complete understanding of the present invention and the advantages thereof, reference is now made to the following description taken in conjunction with the accompanying Drawings in which:

FIG. 5 is a flow diagram illustrating the manner in which the control processor operates within the device to provide control signals;

FIG. 6 is a flow diagram illustrating the feedback control loop of the biofeedback stimulation device;

DETAILED DESCRIPTION

Figure 1:
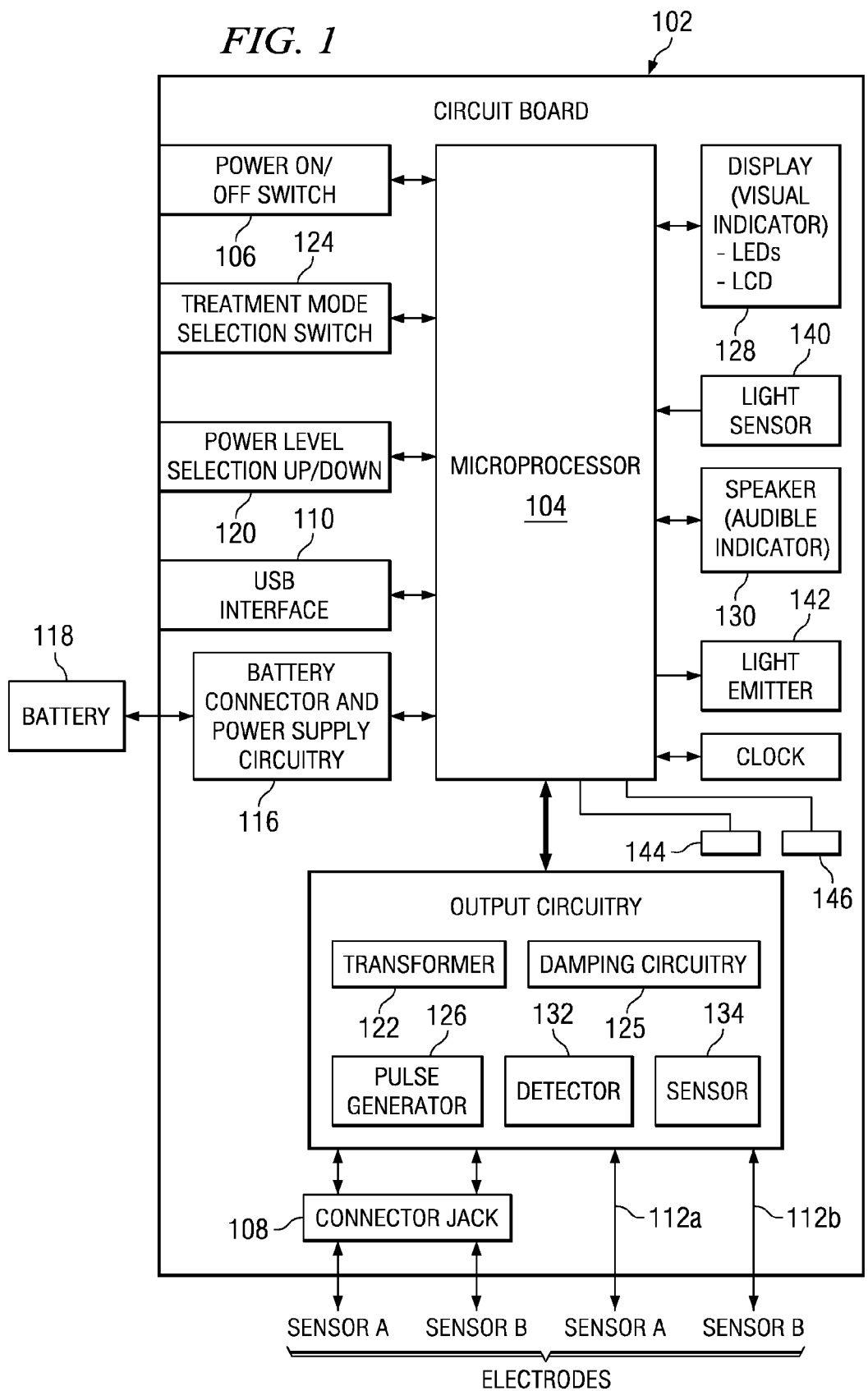
FIG. 1 is a block diagram of a biofeedback stimulation device of the present invention.

Referring now to the drawings, wherein like reference numbers are used herein to designate like elements throughout the various views, embodiments of the present invention are illustrated and described, and other possible embodiments of the present invention are described. The figures are not necessarily drawn to scale, and in some instances the drawings have been exaggerated and/or simplified in places for illustrative purposes only. One of ordinary skill in the art will appreciate the many possible applications and variations of the present invention based on the following examples of possible embodiments of the present invention.

The present invention relates to an electronic device capable of treating pain, such as from inflammation, numbness, tension, injuries and ailments, using biofeedback stimulation to treat the area. The device includes operating modes and controls such that the treatment can be modified as necessary. The device treats the body's electrical system through the application of unique treatment protocols that vary based on the body's own response. The treatment protocols are comprised of combinations of unique waveforms, frequencies and patterns, as well as various wavelengths of light, and magnetic energy.

The device may be composed of a printed circuit board containing electronic components, switches and selectors, a microprocessor, a connector jack for attaching external probes, a set of instructions stored in the microprocessor and a pair of electrodes for delivering the electronic signals to the body and sensing the body's response, a plurality of light sources and one or more light sensors.

The device may provide electronic stimulation to the body using selectable treatment protocols, comprised of combinations of unique waveforms, frequencies and patterns, that are varied based on the response received from the body. The device may relieve pain, by the application of biofeedback stimulation, and direct the body's own resources to promote healing and relief. The device may deliver the biofeedback stimulation in a portable and economical device.

The device may provide improved elements and arrangements thereof in an apparatus for the purposes described which is safe, inexpensive, dependable and fully effective in accomplishing its intended purposes.

Referring now to FIG. 1, there is illustrated a block diagram of the biofeedback stimulation device of the present invention. The device includes a circuit board 102 for containing each of the electronic components. The controlling portion of the device consists of a microprocessor 104. The microprocessor 104 contains a set of stored instructions for controlling the operation of the biofeedback device. The microprocessor 104 in conjunction with other components of the device which will be discussed herein below generate output pulse packets for application to an individual's body. The microprocessor 104 is interconnected with a number of components on the circuit board 102 from which the microprocessor 104 receives inputs from and provides outputs to. An on/off switch 106 provides the user with the ability to turn the entire biofeedback stimulation device on and off. The on/off switch 106 may comprise a standard push button switch or a conventional two position switch in order to place the device in powered and non-powered states. A connector jack 108 enables external probes to be connected to the biofeedback stimulation device. The device also includes a USB port 110 to enable universal serial bus connections to the microprocessor 104. Through the USB connection 110, a USB communications cable may be connected to enable USB communications between the microprocessor 104 and an external device.

A pair of electrodes 112 provide a stimulation signal from the output circuitry 114 and provide a connection point between the biofeedback stimulation device and a body of a user. The output electrodes 112 connect the device to a point on a body of a user. The pair of electrodes 112 additionally provide an input for measuring a body's response to the applied electric signals through the electrodes 112. The output electrodes 112 may have associated therewith outputs of a light emitting circuit 140. The output may be on or surrounding the electrodes 112. A connector 116 enables a battery 118 to be interconnected to the biofeedback stimulation device to power the microcontroller 104 and associated circuitry. The power level selector 120 enables a user to adjust the power level applied to a transformer 122 within the output circuitry 114 by the microprocessor 104 to various levels. The applied power level alters the strength of the stimulation signal output from electrodes 112 to a user's body, Treatment selector switch 124 selects the particular mode of operation for the biofeedback stimulation device. The selected treatment mode from switch 124 provides an indication to the microprocessor 104 of a particular operating mode. The microprocessor 104 configures the pulse generator circuitry 126 to provide a desired pulse output configures the light emitting circuitry 140 to the desired photonic radiation and configures the magnetic circuitry 144 to emit desired magnetic energy according to the selected mode of operation. A series of display LEDs and/or LCDs 128 provide a visual indication of the power level of the device, the mode of operation or other device status. Additionally, a speaker 130 may be used to provide audible indicators to a user of various operating conditions. Various visual and audible indications are provided by the LEDs and LCDs 128 or the speaker 130. These instructions include a mode indication, a power level indication, a battery power indication, a sensor connection indication, a body response status, a time status, body measurement readings, USB interface status, instructional information, treatment status, or diagnosis information. The transformer circuit 122 is energized by signals from a pulse generator circuit 126

The output circuitry 114 is connected to and controlled by the microprocessor 104 to generate output pulses in a stimulation signal through the electrodes 112. The output circuitry 114 also receives feedback signals from the electrodes 112 to control the operation of the microprocessor 104. A transformer 122 generates a signal including packets of one or more pulses responsive to removal of an applied current from the transformer 122 controlled by the microprocessor 104.

The transformer circuit 122 is energized by signals from a pulse generator circuit 126. The output pulses provided from the transformer may be clamped by damping circuitry 125. The various characteristics of the pulse generated by the pulse generator 126 are controlled responsive to control inputs from the microprocessor 104. A detector circuit 132 is responsible for detecting the zero crossing of the pulse signals provided at the electrodes 112. The time between the zero crossing are used by the microprocessor 104 to determine when the device may be removed from the body. The sensor circuit 134 provides the measurements for the zero crossings.

A light sensor 140 detects and measures the reflectance from the body tissues of a patient to which photonic radiation is being provided. The characteristics of the reflectance may be used to provide information to the microprocessor 104 such that the frequency and wavelength of light being emitted by a light emitter 142 may be altered responsive to the detected light reflectance. This feedback loop is designed such that when the frequencies of light and/or wavelengths emitted by the light emitter 142 cause physiological changes within the tissues of a patient, these physiological changes may then be reacted to based upon the changed reflectance of these tissues detected by the light sensor 140. The light emitting circuitry 142 may be controlled by the microprocessor 104 to emit light waves having various different waveforms, frequencies and wavelengths. The light emitter 142 may be configured to emit the light energy either through or around the electrode 112 in order to provide additional therapeutic effects to the electrical stimulus that is provided by the electrodes.

The light emitter 142 may comprise any number of light emitting sources such as an LED, a laser, an electro luminescent fiber, wire or wave guide. An LED may be used to emit a particular range of frequencies wherein the frequencies of the light may have different characteristics on the body tissues of a patient. LEDs may emit light in the range from invisible ultraviolet through infrared and above depending upon the type of LED utilized. A laser may be used to emit a range of frequencies that cover the entire spectrum of frequencies producible by lasers. As described previously, the light emitter 142 may be configured to emit light in the area of the electrodes providing the electro stimulation to a patient's body or additionally may be administered by a separate electro luminescent fiber, wire, or light guide to any other part of the body. The light emitting circuit 142 may emit the light to the patient in a pattern that may or may not track the electro stimulation pattern provided by the electrodes 112.

The electrodes 112 may additionally be magnetic in nature and made from rare earth magnets or other magnetically permeable combinations. The magnetic electrodes may be magnetized by some type of magnetic circuitry 144 including coils or a straight magnet. In this way, in addition to the electrical stimulation signals and the light stimulation signals applied by the biometric feedback device, the patient may apply magnetic therapies to portions of their body. The magnetically applied signals to the body of the user may be altered by control signals to the magnetic circuitry 144 by the microcontroller 104 in response to feedback signals obtained from electromagnetic signals from the bodies detected through the electrodes or from signals provided by the light sensor 140. Magnetic sensors 146 may also be utilized to detect changes in the magnetic fields or emissions of the body having magnetic signals applied thereto.

Figure 2:
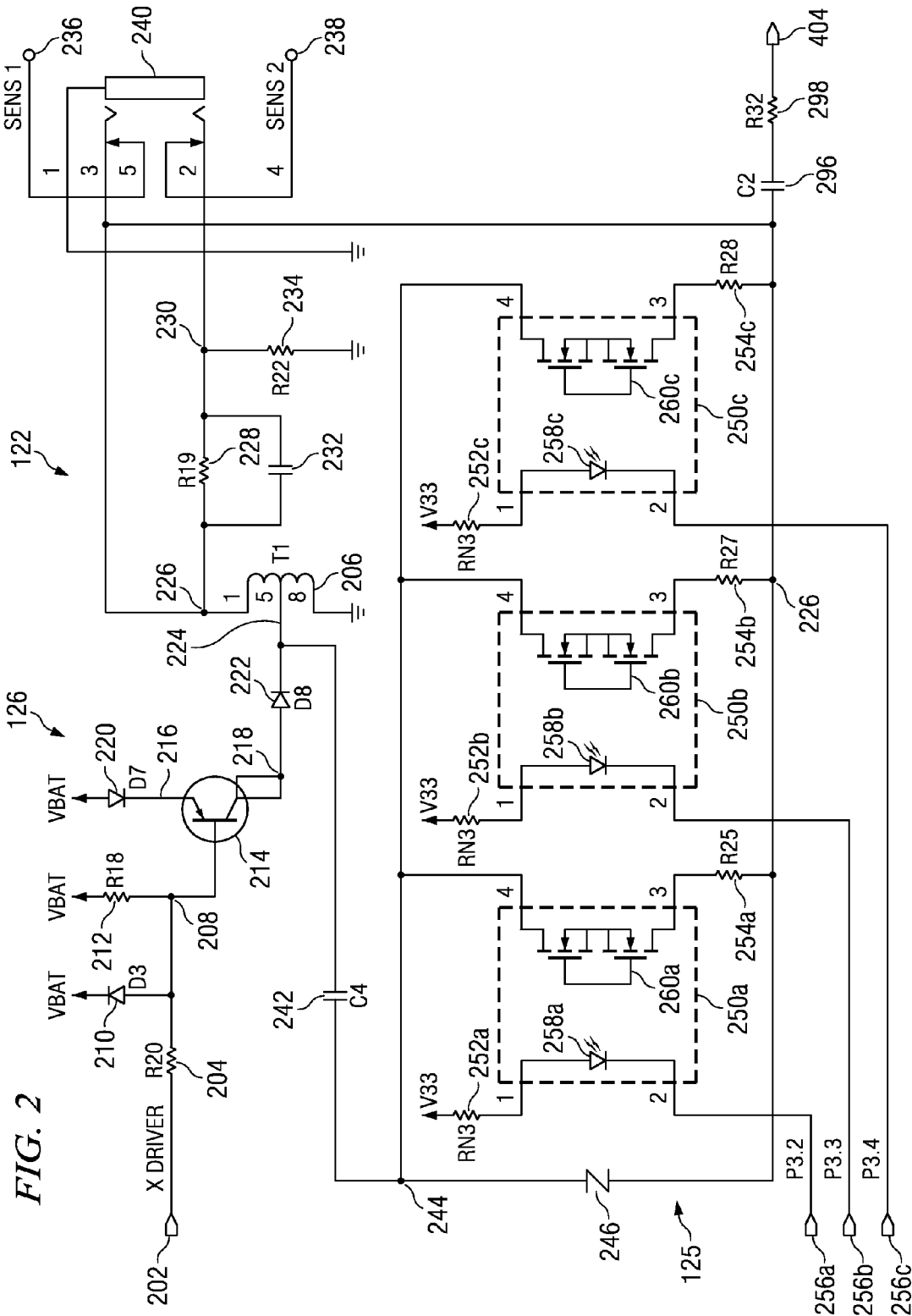
FIG. 2 is a schematic diagram of the transformer circuit and associated transformer shunt.

Referring now to FIG. 2, there is illustrated a schematic diagram of the transformer circuitry 122, the pulse generator circuitry 126 and the damping circuitry 125. A charging current is applied at input 202 to resistor 204. The charging current is provided from the level translator circuit 270 (FIG. 2a) under control of the microprocessor 104. The charging current provides energy to a transformer 206 for generating the stimulation signal. Resistor 204 is also connected to node 208. An anode of diode 210 is connected to node 208 and the cathode of diode 210 is connected to $V_{Batt}$. A resistor 212 is connected between $V_{Batt}$ and node 208. The base of transistor 214 is connected to node 208 and the emitter-collector path of transistor 214 is connected between node 216 and node 218. A diode 220 has its anode connected to $V_{Batt}$ and its cathode connected to node 216. A diode 222 has its anode connected to node 218 and its cathode connected to a center tap 224 of transformer 206. One side of transformer 206 is connected to ground, and the opposite side of transformer 206 is connected to node 226. When a charging current is applied to node 202, transistor 214 is turned on causing a current to be applied to the center tap 224 of transformer 206 by the pulse generator circuitry 126 and begin energizing the transformer.

A resistor 228 is connected between node 226 and node 230. In the preferred embodiment, the resistor 228 has a value of 150 kilo ohms. A capacitor 232 is in parallel with resistor 228 between nodes 226 and 230. In a preferred embodiment, the capacitor 232 has a value of 500 picofarads. This capacitor can eliminate the need for the damping device 246 discussed below by limiting the amplitude of pulses generated by the transformer 206. A resistor 234 is connected between node 230 and ground. Sensor one output 236 is connected to node 226. Sensor two output 238 is connected to node 230. An external sensor 240 is connected between node 226 and node 230. The transformer circuitry 122 is interconnected with the damping circuitry 125 via a capacitor 242. The capacitor 242 is located between the center tap 224 and node 244 of the damping circuitry 125.

The damping circuitry 125 includes a clamping device 246 located between node 244 and node 226. The clamping device 246 prevents the pulses generated when the current is released from the transformer 206 from exceeding a particular amplitude. In a preferred embodiment, the clamping device 246 comprises a bidirectional rectifying diode. The remaining portion of the pulse generator circuitry 126 consists of a transformer shunt enabling the load applied across the transformer 206 to be adjusted by switching a resistance into and out of the load applied to the transformer 206. The transformer shunt consists of three relays 250 which switch a resistor load 254 into and out of the circuit. Each relay 250 has four connections. A first connection is connected to a resistor 252 that is also connected to the system voltage. The relays 250 have a second connection to a load resistor 254 connected between the relay and node 226. Another connection of the relay 250 is connected to control inputs 256 from the microprocessor 104. A light emitting diode 258 is connected between the connection to resistor 252 and the input connected to the control input 256. The light emitting diode 258, when lit actuates a pair of photo sensitive transistors 260 connected between third and fourth inputs of the relay 250. When a control signal is applied to input 256 of one of the relays 250, the light emitting diode 258 causes the actuation of the photo sensitive transistor pair 260 which switches the resistor 254 of the transformer shunt across the transformer 206. As can be seen, there are three relays 250 enabling eight different combinations of the resistors 254 to be switched across the transformer 206 responsive to control signals applied to lines 256a through 256c. Using these various combinations of relays 250, the microprocessor 104 controls the shape and configuration of the packet of pulses output by the transformer in a number of fashions which will be discussed more fully herein below such that the stimulation signal may be configured in a number of desired modes responsive to user inputs. While only three relays 250 are described with respect to the present embodiment, any number of relays 250 may be used.

Figure 2A:
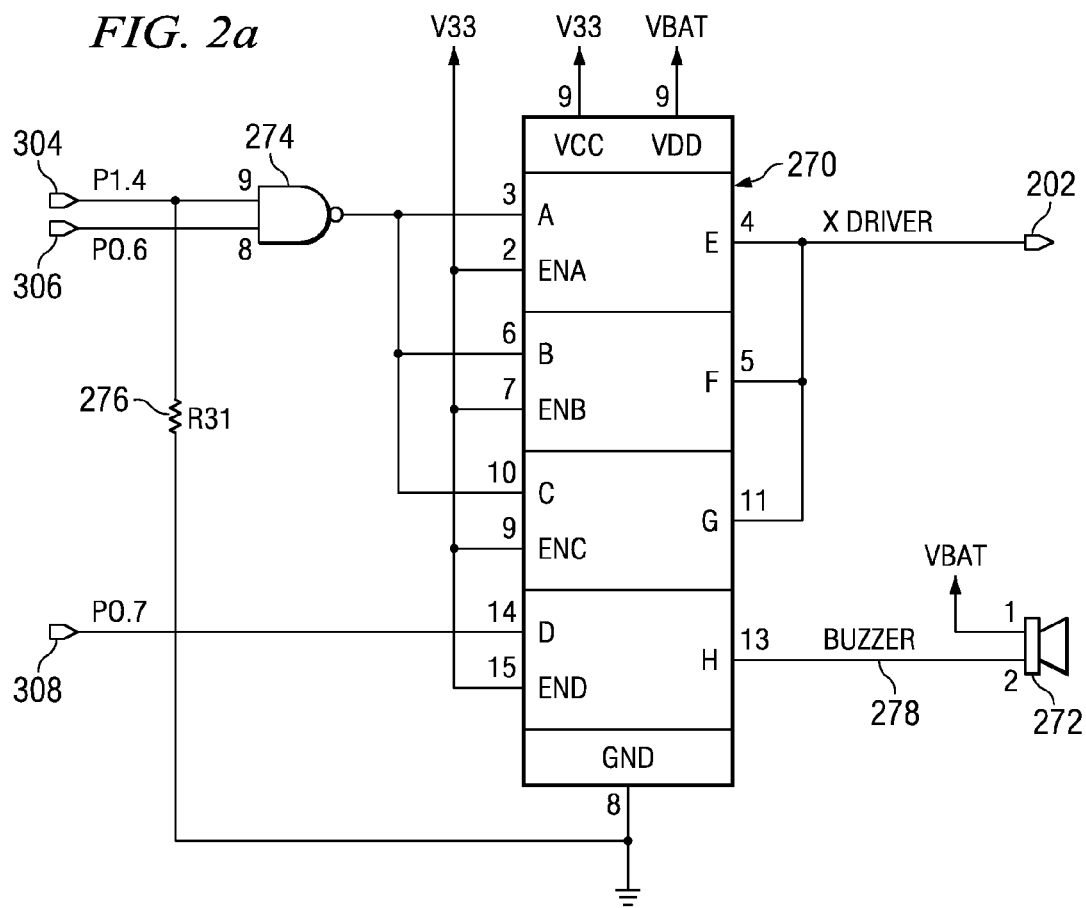
FIG. 2a is a schematic diagram of the level translator circuitry.

FIG. 2a illustrates the level translator circuit 270 for generating the transformer charging signal on line 202. The transformer charging signal is generated by the level translator 270 responsive to control inputs 304 and 306 applied to first and second inputs of a NAND gate 274. The output of the NAND gate 274 is provided to three separate inputs of the level translator 270. A resistor 276 is connected between the input of NAND gate 274 connected to control input 304 and ground. An audio speaker 272 is connected to receive an audio signal from the level translator circuit 270 on line 278 responsive to a control input 308 from the microcontroller 104.

Figure 3A:
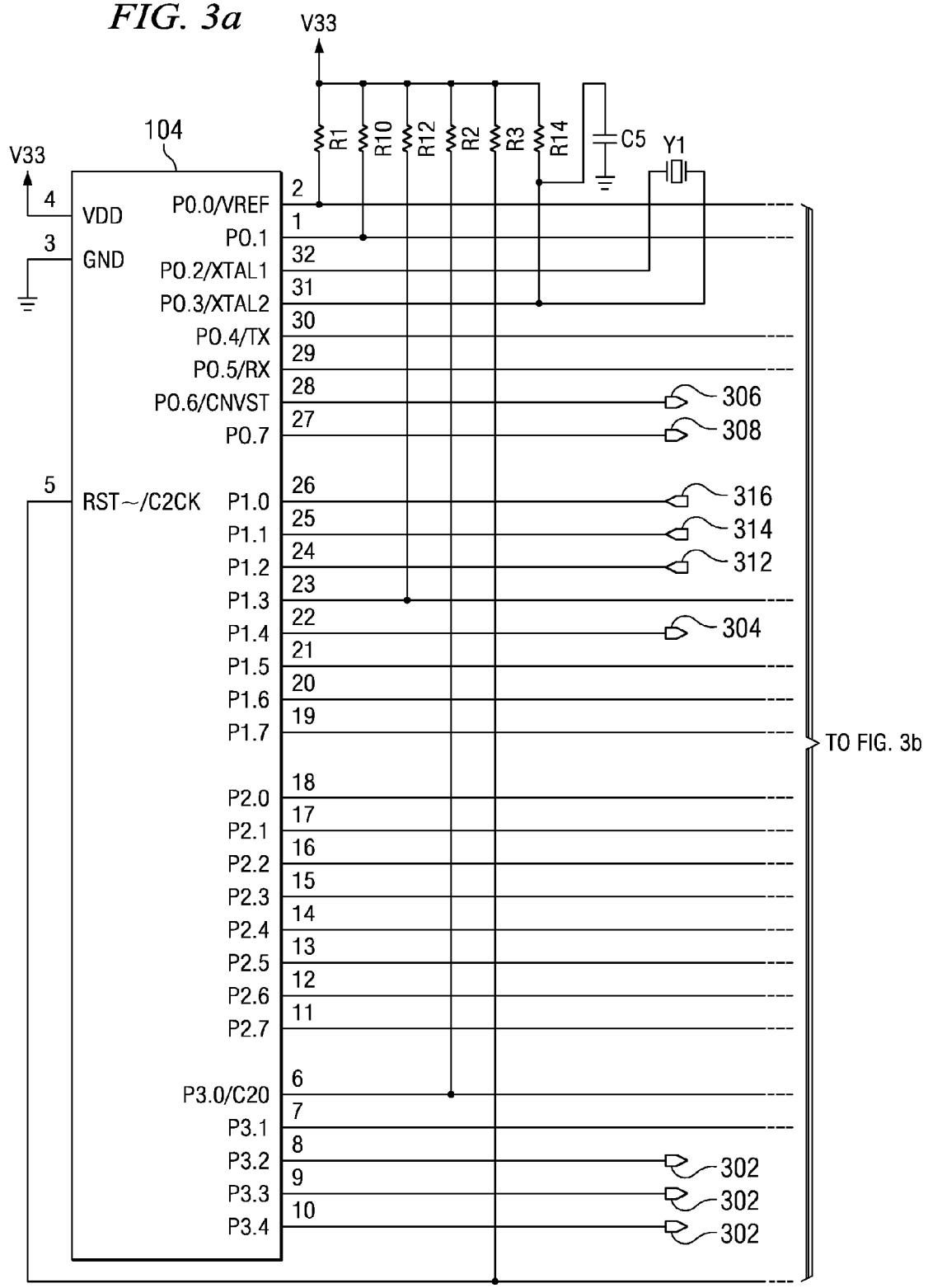
FIG. 3a-3b is a schematic diagram of the microcontroller of the device.
Figure 3B:
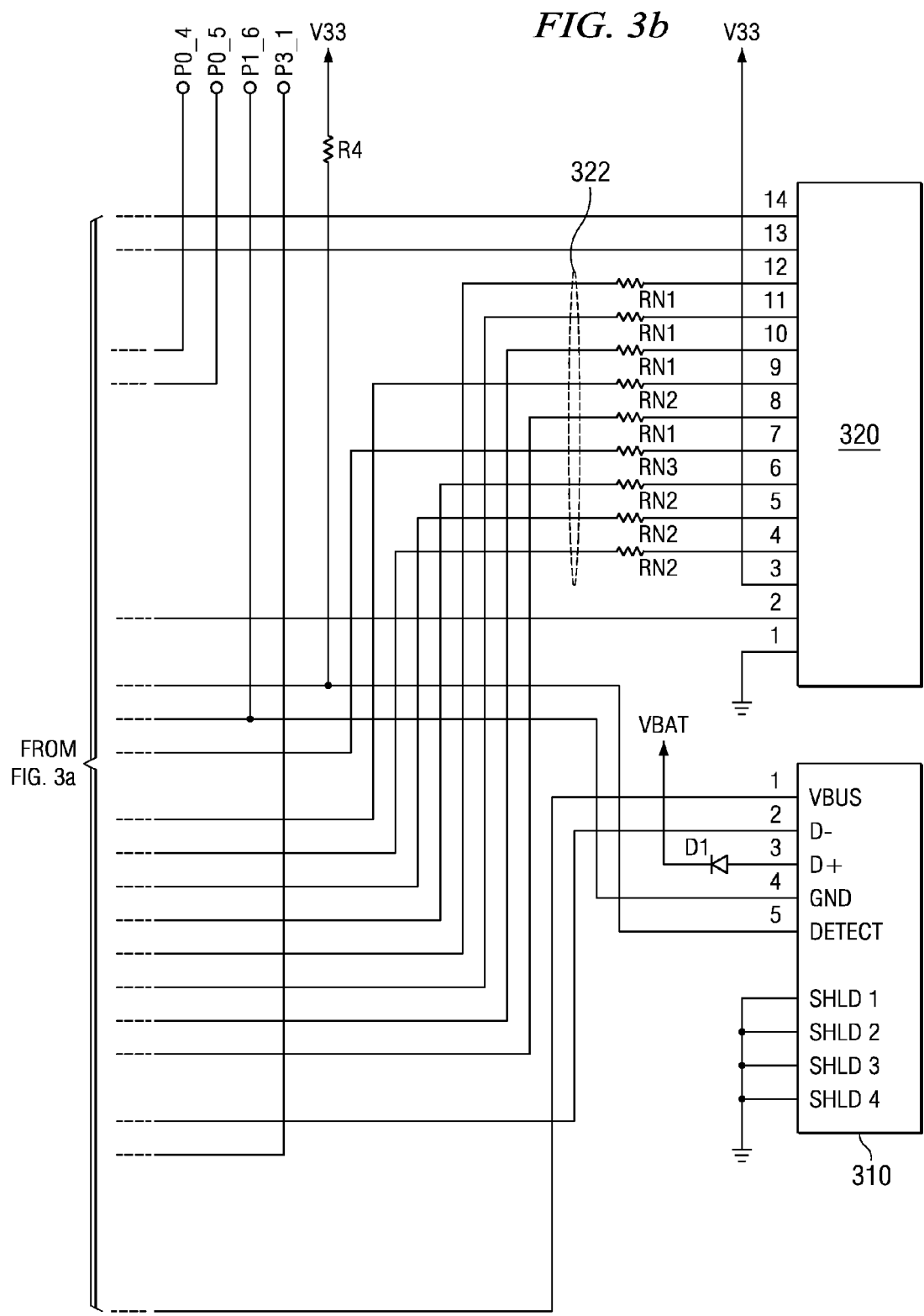

Referring now to FIGS. 3a-3b, there is illustrated the microprocessor 104 for controlling the biofeedback stimulation device described herein. The microprocessor 104 provides three control outputs 256 for controlling the transformer shunt relays 250 described previously. As described herein above, these signals enable the control of the configuration of the pulse packages generated from the transformer 206. Control outputs 304, 306 and 308 provide control signals to the level translator 270 to control the provision of the transformer charging signal on output 202 responsive to control signals 304 and 306 and to control the audio output to speaker 272 via control output 308. An LED circuit 320 receives a number of control outputs 322 from the microprocessor 104 to provide various visual indicators to the user of the biofeedback stimulation device.

Figure 4:
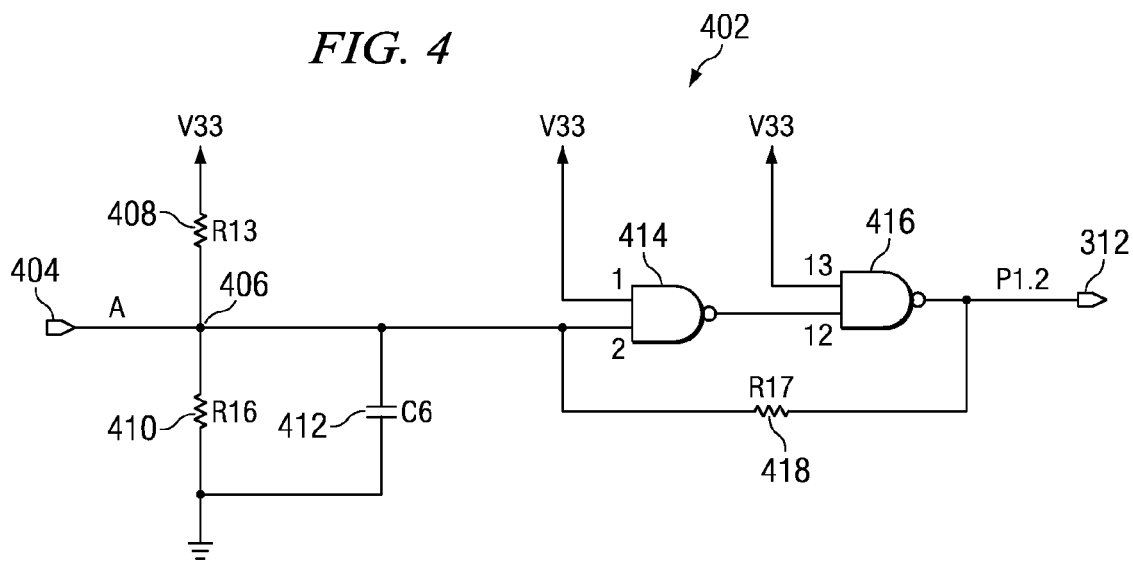
FIG. 4 is a schematic diagram of the detector circuit of the device.

Control input 312 receives an input control signal from the detector module 132 as described in FIG. 4. The detector module 132 is responsible for determining the number of zero crossings for pulse signals generated within signal packets provided by the transformer 206. The input 404 of the detector module 132 is connected to node 226 on one side of the transformer 206 through capacitor 296 and resistor 298. The input 404 is connected to node 406 of the detector 132. A resistor 408 is connected between node 406 and system power. A second resistor 410 is connected between node 406 and system ground. A capacitor 412 is in parallel with resistor 410 between node 406 and ground. A first input of NAND gate 414 is connected to node 406. The second input of NAND gate 414 is connected to system power. The output of NAND gate 414 is connected to a first input of NAND gate 416. The second input of NAND gate 416 is connected to system power. The output of NAND gate 416 is connected to control input 312 from the microprocessor 104. A resistor 418 is connected between the input of NAND gate 414 connected to node 406 and to the output of NAND gate 416. Control inputs 314 and 316 are connected to a battery sensor circuit.

The processor may use the control signals to control a number of processes within the device. The processor may control the amount of damping applied to each pulse. The processor may also control the stimulation pulse applied by the pulse generator to the transformer and the power or pulse width of the stimulation pulse. The processor may also control the frequency and wavelength of the photonic and magnetic radiation that are applied. Control signals may also be generated responsive to the analysis of patterns in a response signal from the body and altered in real time. The altered control signals may generate a pulse that drives the response from the body to a desired outcome. The analysis may also be communicated to the user or a data collection apparatus along with any derived information.

The generation of control signals by the microprocessor 104 is more fully described with respect to the flow diagram illustrated in FIG. 5. Initially, at step 502, the microprocessor 104 determines the selected mode of operation of the biofeedback stimulation device responsive to inputs received from the treatment mode selection switch 124 and the power level selection switch 120. From the selected mode and power level, the microprocessor 104 determines the appropriate control signals to be applied to the relays 250 of the damping circuitry 125 and to the light emitting circuitry 142 and magnetic circuitry 144 and applies these control signals at step 504. The microprocessor 104 also determines and applies at step 506 the appropriate control signals 125 to charge the transformer 206 via the level translator 270. This is accomplished by applying the appropriate control signals at step 506 to the level translator circuit 270. The control signals are continuously applied to the transformer 206, to the light emitter 142 and/or magnetic circuitry 144 at step 506 until inquiry step 508 determines a release point has been received responsive to the applied control signals from the microprocessor 104.

Once inquiry step 508 determines to release either of the control signals applied to the transformer 206, the light emitter 142, or the magnetic circuitry 144, the microprocessor modifies the control signals applied to the transformer shunt and to the light emitting circuitry 142 at step 509 to modify the electrical light and magnetic stimulation signals as desired. In some embodiments, the control signals applied may remain constant and the control signals will not be modified at step 509. The microprocessor 104 next monitors the feedback provided from the electrodes 112 that are providing the electronic stimulation signal to the body of a user and from the light sensor 140 detecting the light reflectance from the body of a user. The specifics of feedback detection will be more fully discussed with respect to FIG. 6. Inquiry step 512 determines if the feedback received by the microprocessor has remained constant for a selected period of time. If not, the microprocessor continues to detect the feedback at step 510. Once inquiry step 512 determines that the feedback is constant for a selected period of time, some type of notification is provided at step 514 to the user of the biofeedback stimulation device. This notification may take the form of an audio indicator such as a beep played through speaker 272 or some type of visual indicator through one of the LEDs or LCD displays 128. The microprocessor 104 monitors for a shut down indication by the user powering off the device at inquiry step 516. Inquiry step 516 continues to monitor for some type of shut down signal until it is received. Upon receipt of a shut down signal, the microprocessor turns off the device at step 518.

Referring now to FIG. 6, there is illustrated the manner in which the microprocessor 104 monitors the feedback from the electrodes 112 which are applying the electronic stimulation signal to an individual's body and detecting feedback from the body. The feedback determined by the microprocessor 104 comprises a determination of the time between zero crossings of the electronic stimulation signal. The time between the zero crossings of the pulses will alter based upon the resistance provided by the body to which the device has been attached. As the resistance in a person's body decreases, the time between zero crossings of the pulses of a packet will alter. Once the resistance is steady, the time between zero crossings of the pulses will remain constant and the treatment regimen may be stopped.

Once the time between the zero crossings of pulses is determined at step 602, this time value is stored within a memory associated with the microprocessor 104 at step 604. Inquiry step 606 determines if a count value is equal to a predetermined value that is used for averaging a number of time values. If not, control passes back to step 602. Once the appropriate number of time values have been stored and count is equal to the preselected value at inquiry step 606, the average time between the zero crossings of pulses may be determined at step 608. This value may be compared with a previously determined value at inquiry step 610 to determine if the determined average time value is constant. If the determined average time value is not constant, count is reset to zero at step 612 and control passes back to step 602. If it is determined that the stored time value is constant with a previously stored time value, inquiry step 614 determines if the successive number of average time values have been constant for a selected period Y. If not, count is reset to zero and control returns to step 602. Once the average time values have been constant for a selected period of time as determined at inquiry step 614, an indicator is generated to the user indicating the device may be shut down at step 616. In an alternative embodiment, the indicator could cause the device to automatically shut down rather than waiting for a user provided shut down signal.

The microprocessor may further make adjustments in the control signals applied to the light emitter circuitry 142 responsive to the signals detected by the light sensor 142. As described previously, responsive to detections of changes in the reflectance of light from the body tissues, the waveforms and wavelengths applied by the light emitter 142 may be altered to achieve different therapeutic results.

Figure 7:
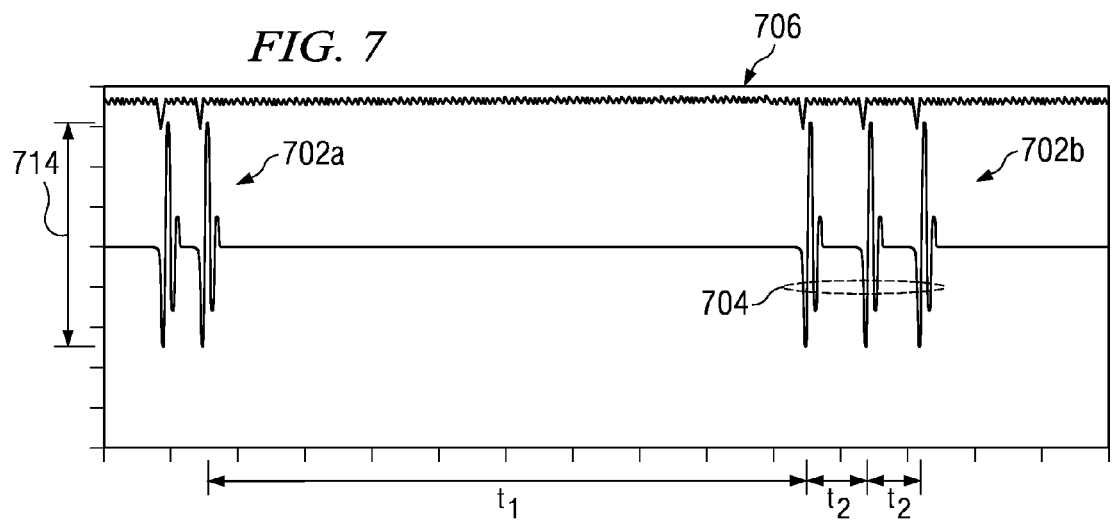
FIG. 7 illustrates the stimulation signal generated by the biofeedback stimulation device, and the various manners in which the packets and pulses may be controlled.

Referring now to FIG. 7, the control values provided to the transformer shunt circuitry to the light emitting circuitry 142 and to the magnetic circuitry 144 may be used to configure packets 702 of pulses 704 which are transmitted in an electronic, light or magnetic stimulation signal 706. Using the control signals, the packets 702 of pulses 704 are controlled in a number of manners. In one embodiment, a time $t_1$ between a first packet 702a and a second packet 702b may be controlled using the control signals applied to the level translator circuit 270 m light emitter 142 and magnetic circuitry 144. The time $t_1$ may be varied between adjacent packets or held constant. The microprocessor 104 may also control the number of pulses 710 located within a particular packet 702. The number of pulses 710 may be randomly varied between packets, gradually increased/decreased between packets or maintained constant. The size of the packet 702 may be extended or reduced by altering the number of pulses 704 within a packet 702 through use of the applied control signals to the pulse generation circuitry 126, light emitter 142. and magnetic circuitry 144. The pulses may be varied from any number from 1-n. Within the stimulation signal the size of packets 702 may be varied or constant.

The microprocessor 104 may also control the time $t_2$ between adjacent pulses 704 of a packet 702. This would be an alternative way for increasing or decreasing the size of a particular packet 702 by altering the time $t_2$ between pulses 204 rather than changing the number of pulses per packet 710 as described previously. The time $t_2$ may also be varied in any number of desired fashions. The time $t_2$ between pulses may also be controlled using the control signals to the pulse generation circuitry 126. Additionally, the pulses 704 may be damped such that the amplitude 714 may be increased or decreased to change the magnitude of the pulses 704 provided within the electronic stimulation signal 706. The amplitude 714 is also controlled through the damping circuitry 125 and may be done with a combination of the relays 250 in the damping circuitry 125, the light emitter 142 and the magnetic circuitry 144.

Figure 8A:
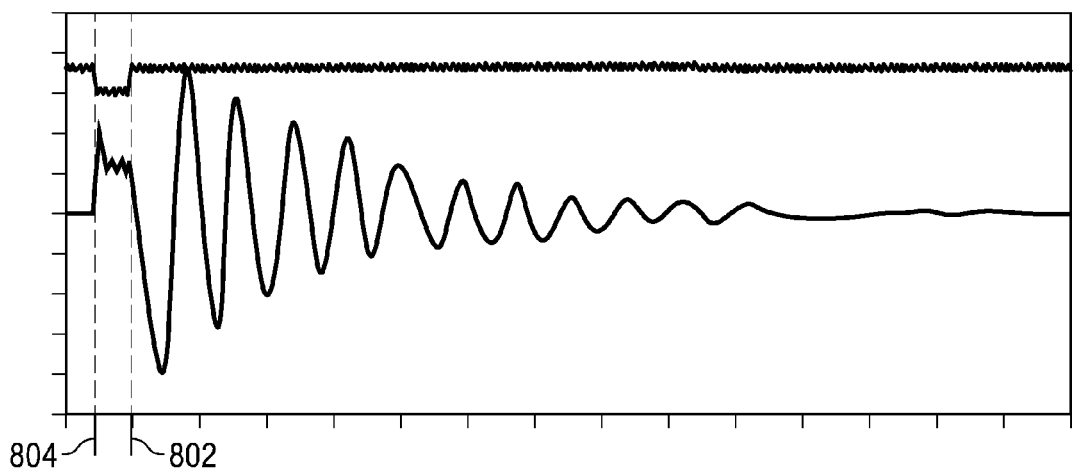
FIGS. 8a-8d illustrate various output signals of the biofeedback stimulation device.
Figure 8B:
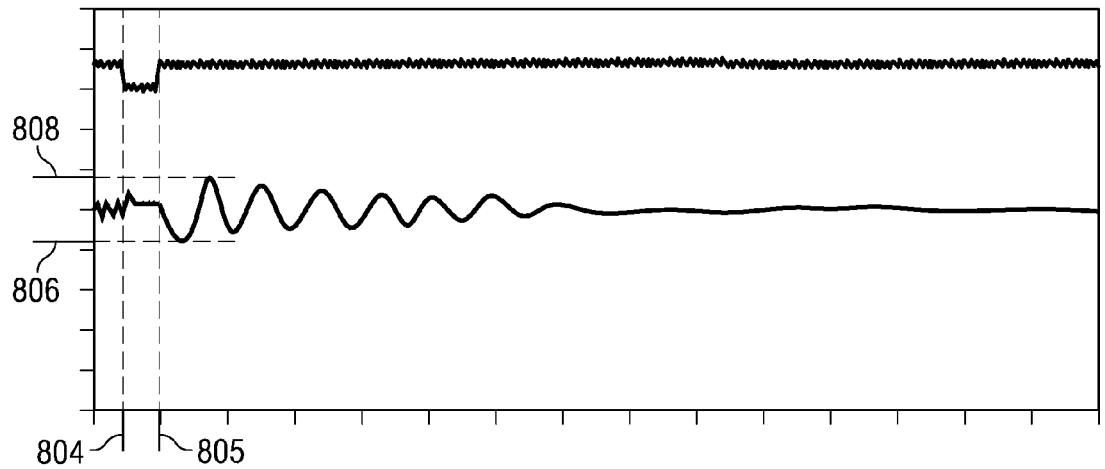
Figure 8C:
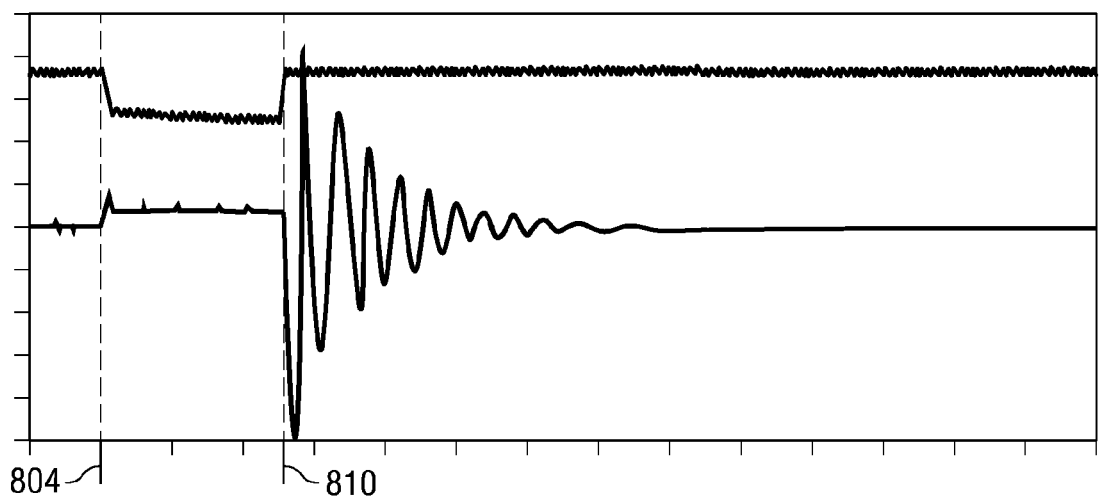

Referring now to FIGS. 8a through 8d, there are illustrated a number of pulse waveforms that illustrate the variety of outputs that may be achieved from the biofeedback stimulation device described herein above. While the creation of electronic pulses are described, similar light and magnetic wavelengths may be created. FIG. 8a illustrates a first pulse wherein the charging signal has been applied for a medium amount of time and released from application to the transformer at point 802. The output of the transformer begins the fly back oscillation mode creating the oscillations in the positive and negative directions with a steadily decreasing magnitude for the oscillation. The time period that the charging signal is applied between 804 and 802 controls the amplitude of the modulations of the output. By varying the release point 802, the amplitude of the output pulse may be increased or decreased. A situation wherein the amplitude of the output pulse is decreased is illustrated in FIG. 8b. In this figure, the charging time is held between points 804 and point 805. Due to the shorter magnitude of the application of the charging signal, the amplitude of the oscillation of the output signal between 806 and 808 is decreased. Referring now to FIG. 8c, there is illustrated a situation wherein the charging signal is applied between points 804 and 810 for a longer period of time, causing the amplitude of the output pulse to increase.

Figure 8D:
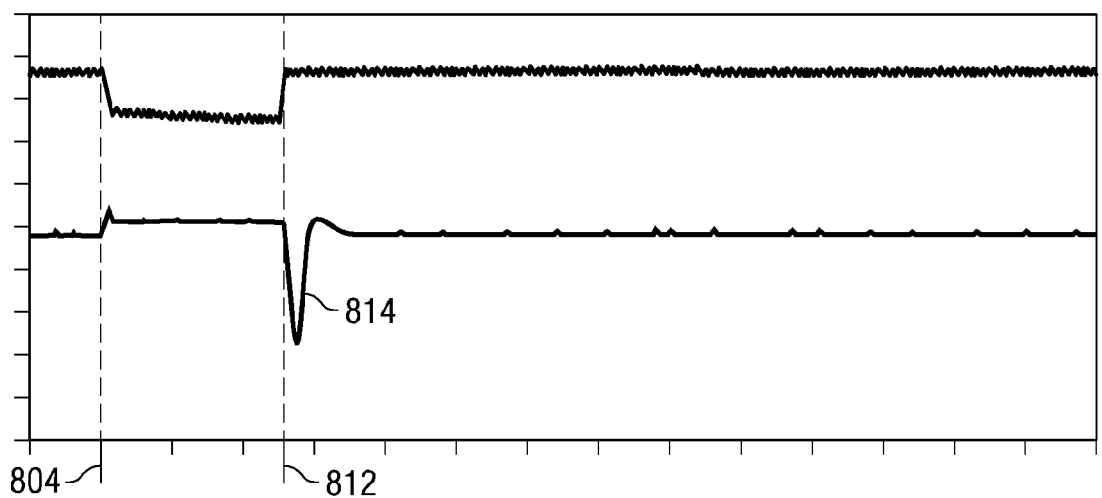

In addition to controlling the amplitude of the output by controlling the release point of the charging signal to the transformer, the damping circuit may be used to control the output pulse in the manner illustrated in FIG. 8d. In this case, the charging signal is applied between points 804 and 812. In this case, the output signal generates a single oscillation 814 in the negative direction that then approaches zero rather than oscillating in the positive direction. This may be achieved by applying the appropriate load across the output of the transformer using the damping circuitry 125.

Therefore, using the above-described device, a user may strategically apply an electronic light and magnetic stimulation signal to specific parts of their body and by the use of mode selection buttons, may control the configuration of the packets of pulses applied to their body. The pulses may be adjusted in any of the fashions discussed herein above.

Utilizing the above described circuitry, varying combinations of electrical stimulation, light stimulation and magnetic stimulation may be applied to a patient's body to achieve therapeutic effects associated with the application of these various energies to the body. The application of the various energies may be done in any combination wherein only one or a combination of the energies can be applied to the body at any particular time to achieve differing therapeutic effects.

It will be appreciated by those skilled in the art having the benefit of this disclosure that this invention provides a biofeedback stimulation device. It should be understood that the drawings and detailed description herein are to be regarded in an illustrative rather than a restrictive manner, and are not intended to limit the invention to the particular forms and examples disclosed. On the contrary, the invention includes any further modifications, changes, rearrangements, substitutions, alternatives, design choices, and embodiments apparent to those of ordinary skill in the art, without departing from the spirit and scope of this invention, as defined by the following claims. Thus, it is intended that the following claims be interpreted to embrace all such further modifications, changes, rearrangements, substitutions, alternatives, design choices, and embodiments.

What is claimed is:

1. A biofeedback stimulation device, comprising:
   a user interface for providing at least one input signal;
   a processor for generating a first control signal and a plurality of second control signals responsive to the at least one input signal;
   transformer stimulation circuitry for generating an electrical stimulation signal including packets of at least one pulse responsive to the first control signal;
   damping circuitry for configuring the at least one pulse in the packets to a selected one of a plurality of configurations responsive to the plurality of second control signals;
   output electrodes for applying the at least one pulse in the packet of the electrical stimulation signal to a user;
   detector circuitry for detecting zero crossings of the at least one pulse in the packet of the electrical stimulation signal;
   wherein the processor further causes generation of an indicator responsive to the detected zero crossings, wherein the application of the electrical stimulation signal and a light stimulation signal are controlled by the at least one control signal; and
   second circuitry for generating and detecting the light stimulation signal.

2. The biofeedback stimulation device of claim 1, wherein the circuitry further also enables an application of a magnetic stimulation signal to the body of the individual, wherein the magnetic stimulation signal is controlled by the at least one control signal.

3. The biofeedback stimulation device of claim 1, wherein the second circuitry further comprises:
   light emitter circuitry for generating photonic radiation for application to the body of the individual as the light stimulation signal responsive to a first control signal of the at least one control signal; and
   light sensor circuitry for detecting reflectance from the body of the individual and generating a feedback signal responsive thereto.

4. The biofeedback stimulation device of claim 3, wherein the processor generates the first control signal responsive to the feedback signal.

5. The biofeedback stimulation device of claim 3, wherein the light emitter circuitry comprises an LED.

6. The biofeedback stimulation device of claim 3, wherein the light emitter circuitry comprises a laser.

7. The biofeedback stimulation device of claim 3, wherein the light emitter circuitry further includes at least one of an electroluminescent fiber, wire or light guide.

8. The biofeedback stimulation device of claim 3, wherein the light emitter circuitry generates photonic radiation at one of a plurality of wavelengths and one of a plurality of frequencies responsive to the first control signal.

9. The biofeedback stimulation device of claim 3, wherein the first circuitry further includes electrodes for applying the electric stimulation signal.

10. The biofeedback stimulation device of claim 9, wherein the light emitting circuitry emits light from the electrode.

11. The biofeedback stimulation device of claim 10, wherein the light emitting circuitry emits light from around the electrode.

12. A biofeedback stimulation device, comprising:
   a user interface for providing at least one input signal;
   a processor for generating a first control signal and a plurality of second control signals responsive to the at least one input signal;
   transformer stimulation circuitry for generating an electrical stimulation signal including packets of at least one pulse responsive to the first control signal;

damping circuitry for configuring the at least one pulse in the packets to a selected one of a plurality of configurations responsive to the plurality of second control signals;

output electrodes for applying the at least one pulse in the packet of the electrical stimulation signal to a user;

detector circuitry for detecting zero crossings of the at least one pulse in the packet of the electrical stimulation signal;

wherein the processor further causes generation of an indicator responsive to the detected zero crossings, wherein the application of the electrical stimulation signal and a light stimulation signal are controlled by the at least one control signal; and second circuitry for generating and detecting the light stimulation signal, said second circuitry comprising:

light emitter circuitry for generating photonic radiation for application to the body of the individual as the light stimulation signal responsive to a first control signal of the at least one control signal; and light sensor circuitry for detecting reflectance from the body of the individual and generating a feedback signal responsive thereto;

wherein the electrical stimulation signal and the light stimulation signal are selectively applied to a body of a user responsive to the at least one control signal.

13. The biofeedback stimulation device of claim 12, further including third circuitry further also enabling a selective application of a magnetic stimulation signal to the body of the individual responsive to the at least one control signal.

14. The biofeedback stimulation device of claim 12, wherein the processor generates the first control signal responsive to the feedback signal.

15. The biofeedback stimulation device of claim 12, wherein the light emitter circuitry comprises an LED.

16. The biofeedback stimulation device of claim 12 wherein the light emitter circuitry comprises a laser.

17. The biofeedback stimulation device of claim 12, wherein the light emitter circuitry further includes at least one of an electroluminescent fiber, wire or light guide.

18. The biofeedback stimulation device of claim 12, wherein the light emitter circuitry generates photonic radiation at one of a plurality of wavelengths and one of a plurality frequencies responsive to the first control signal.

19. The biofeedback stimulation device of claim 12, wherein the first circuitry further includes electrodes for applying the electric stimulation signal.

20. The biofeedback stimulation device of claim 19, wherein the light emitting circuitry emits light from the electrode.

21. The biofeedback stimulation device of claim 19, wherein the light emitting circuitry emits light from around the electrode.

* * * * *